(12) United States Patent
Miller

(10) Patent No.: US 7,662,134 B2
(45) Date of Patent: Feb. 16, 2010

(54) NEEDLE STICK PROTECTION DEVICE

(76) Inventor: Stuart H. Miller, 16 E. Eighth St., Clifton, NJ (US) 07011-1102

( * ) Notice: Subject to any disclaimer, the term of this patent is extended or adjusted under 35 U.S.C. 154(b) by 204 days.

(21) Appl. No.: 11/581,402

(22) Filed: Oct. 17, 2006

(65) Prior Publication Data
US 2007/0055203 A1    Mar. 8, 2007

Related U.S. Application Data

(63) Continuation-in-part of application No. 10/862,585, filed on Jun. 8, 2004, now Pat. No. 7,207,975.

(60) Provisional application No. 60/543,540, filed on Feb. 12, 2004.

(51) Int. Cl.
*A61M 5/32* (2006.01)
(52) U.S. Cl. .............. 604/192; 604/110; 604/198; 604/187
(58) Field of Classification Search ......... 604/192–198, 604/110, 162, 163, 171, 174
See application file for complete search history.

(56) References Cited

U.S. PATENT DOCUMENTS

| | | | |
|---|---|---|---|
| 4,915,702 A | 4/1990 | Haber | |
| 4,917,672 A | 4/1990 | Terndrup et al. | |
| 5,217,438 A | 6/1993 | Davis et al. | |
| 5,295,972 A | 3/1994 | Mischenko | |
| 5,746,215 A | 5/1998 | Manjarrez | |
| 6,406,459 B1 | 6/2002 | Allmon | |
| 6,569,115 B1 | 5/2003 | Barker et al. | |
| 6,595,955 B2 * | 7/2003 | Ferguson et al. | ............ 604/110 |
| 2002/0193745 A1 | 12/2002 | Ferguson | |
| 2003/0060771 A1 | 3/2003 | Bialecki et al. | |
| 2003/0144632 A1 | 7/2003 | Hommann et al. | |

* cited by examiner

*Primary Examiner*—Kevin C Sirmons
*Assistant Examiner*—Phillip Gray
(74) *Attorney, Agent, or Firm*—Welsh & Flaxman LLC

(57) ABSTRACT

A needle stick protection device includes a housing and a locking member positioned within the housing to permit the selective locking and releasing of the needle relative to the housing. The device further includes a self-locking member cooperating with an opening in the housing to permanently secure the tip of the needle for disposal. The self-locking member is longitudinal in shape and includes a plurality if spring biased locking tabs along the length thereof. The spring biased locking tabs extend outwardly from the longitudinal axis of the self-locking member; wherein the locking tabs engage inner wall surfaces of the housing in a locked position preventing removal of the self-locking member from the housing and securing the needle tip permanently within the housing.

9 Claims, 8 Drawing Sheets

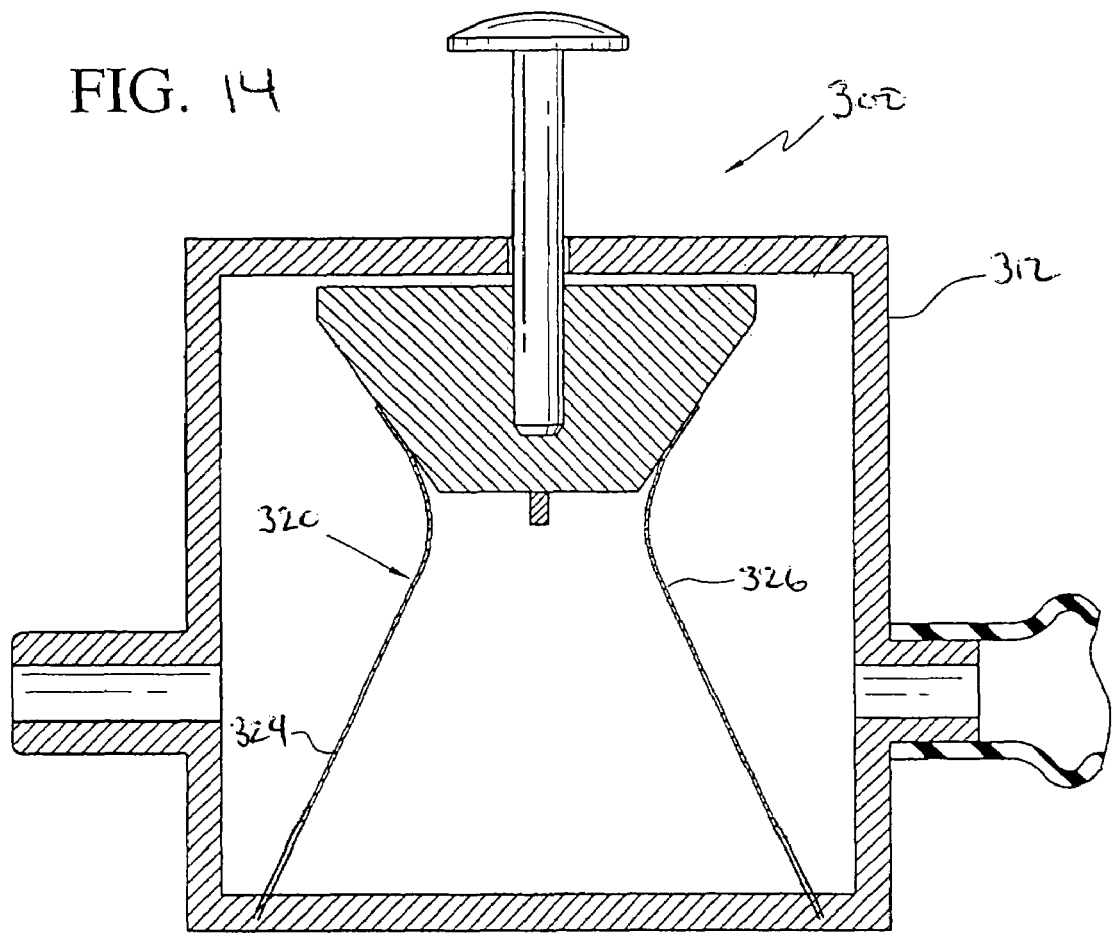

NEEDLE STICK PROTECTION DEVICE

CROSS REFERENCE TO RELATED APPLICATIONS

This application is a continuation-in-part of U.S. patent application Ser. No. 10/862,585, entitled "NEEDLE STICK PROTECTION DEVICE", filed Jun. 8, 2004, which is currently now U.S. Pat. No. 7,207,975, which is based upon U.S. Provisional Patent Application Ser. No. 60/543,540, entitled "Needle Stick Protection Device", filed, Feb. 12, 2004.

BACKGROUND OF THE INVENTION

1. Field of the Invention

The invention relates to a device for preventing needle sticks. More particularly, the invention relates to a device for preventing needle sticks wherein the needle may be selectively locked and released within a needle stick protection device or permanently locked for disposal.

2. Description of the Prior Art

As those within the medical field have developed an understanding that a variety of diseases may be transferred via unclean and previously used needles, a wide variety of devices have been developed for protecting medical practitioners and other individuals from previously utilized needles.

Currently available needle stick protection devices generally operate by either withdrawing the used needle into a hard protective shell or extending a hard protective shell over the used needle. These devices are utilized once and then discarded in an approved collection device.

While most procedures permit the disposal of needles after a single usage, some medical procedures require that needles be used more than once on a patient during a procedure. These used needles may be passed between physicians and other medical practitioners several times during the procedure and, as such, a possibility exists that one other than the patient may be stuck with these contaminated needles during the procedure.

As such, a need exists for a needle stick protection device in which the needle may be selectively shielded and unshielded as the medical procedure dictates. The present invention provides such a needle stick protection device that further includes a member to permanently lock the needle for disposal when the needle is no longer usable.

SUMMARY OF THE INVENTION

The needle stick protection device of the present invention includes a housing and a locking member positioned within the housing to permit the selective locking of the needle relative to the housing. The locking member includes a spring-biased strip having first and second upwardly extending arms connected by a central base member. The first and second upwardly extending arms are biased relative to each other and respectively include a first needle aperture and second needle aperture. A release member is associated with the locking member for facilitating the controlled release of a needle locked in position by the locking member. The release member engages the first upwardly extending arm and the second upwardly extending arm such that selective movement of the release member causes the first and second upwardly extending arms to move between a first locking position in which the first and second upwardly extending arms are angled relative to each other and a second release position in which the first and second upwardly extending arms are substantially parallel. In use, the first and second needle apertures are oriented to permit the free passage of a needle therethrough when the locking member is in its second release position and the first and second needle apertures are oriented to lock the needle relative to the locking member when the first and second upwardly extending arms are in their first locking position. This locking and unlocking procedure may be repeated using the device of the present invention as many times as is called for during the protocol of the particular medical procedure being performed. When the procedure is complete, the needle stick protection device includes at least one self-locking member that prevents the downward movement of the of the release member thereby preventing unlocking of a captured needle leaving it permanently secured within the needle stick protection device. This enables the device to be disposed of without any danger of exposing the needle. The self-locking member has an elongated shape and includes at least one spring biased locking tab along its longitudinal axis that engages the housing of the needle stick protection housing preventing withdrawal of the self-locking member and permanently securing it in a position to block movement of the release member.

It is also an object of the present invention to provide a needle stick protection device that provides locking and unlocking of a needle within the needle stick protection device enabling re-use of the needle and also provides a permanent locking of the needle within the needle stick protection device for disposal when the needle is no longer used.

It is another object of the present invention to provide a permanent needle-locking member in a needle stick protection device having integral locking tabs to permanently position the locking member.

It is a further object of the present invention to provide a permanent needle-locking member that is attached to the housing of the needle stick protection device and manually positioned to a permanent locking location.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 14 is a cross sectional view of a needle stick protection device in accordance with an alternate embodiment.

DESCRIPTION OF THE PREFERRED EMBODIMENTS

Figure 1:
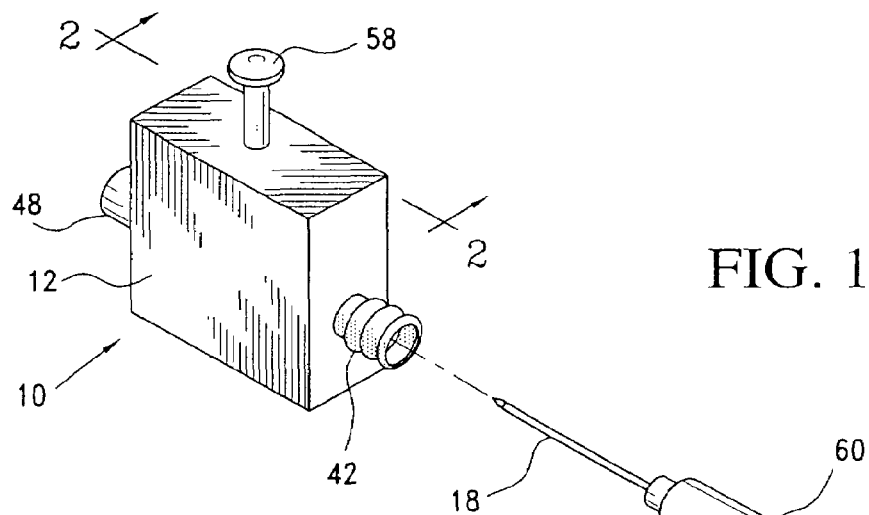
FIG. 1 is an exploded perspective view of the present needle stick protection device.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to FIGS. 1 to 5, a needle stick protection device 10 is disclosed. The protection device 10 includes a housing 12 having first and second apertures 14, 16 shaped and dimensioned for permitting the free passage of a needle 18 through the housing 12. The protection device 10 further includes a locking member 20 positioned within the housing 12 to permit the selective locking of the needle 18 relative to the housing 12. The locking member 20 includes a spring-biased strip 22 having first and second upwardly extending arms 24, 26 connected by a central base member 28. The first and second upwardly extending arms 24, 26 are biased toward each other and respectively include a first needle aperture 30 and a second needle aperture 32.

The protection device 10 also includes a release member 34 associated with the locking member 20 for facilitating the controlled release of a needle 18 locked in position by the locking member 20. The release member 34 includes a camming member 36 extending between the first upwardly extending arm 24 and the second upwardly extending arm 26. The camming member 36 includes a first tapered side 38 and a second tapered side 40. The first and second camming surfaces 38, 40 respectively engage the first upwardly extending arm 24 and the second upwardly extending arm 26 such that selective movement of the camming member 36 causes the upwardly extending arms 24, 26 to move between a first locking position (see FIG. 4) in which the first and second upwardly extending arms 24, 26 are angled toward each other and a second release position (see FIG. 3) in which the first and second upwardly extending arms 24, 26 are substantially parallel.

In use, the first and second needle apertures 30, 32 are oriented to permit the free passage of a needle 18 therethrough when the locking member 20 is in its second release position and the first and second needle apertures 30, 32 are oriented to lock the needle 18 relative to the locking member 20 when the first and second upwardly extending arms 24, 26 are in the first locking position. The locking member 20 is shaped and dimensioned to fix the position of the needle stick protection device 10 at any axial location along the length of the needle 18. With the tip of the needle 18 positioned within the housing 12, bodily contact is prevented. The release member 34 is utilized in shifting the locking member 20 to its second release position, unlocking the needle stick protection device 10 so that the needle stick protection device 10 may slide to any axial location along the length of the needle 18. Finally, and as will be discussed below in greater detail, the protection device 10 includes a bellows seal 42 adapted to prevent bodily contact with the portion of the needle 18 positioned directly behind the housing 12 and to prevent the needle stick protection device 10 from sliding off the end of the needle 18.

In accordance with a preferred embodiment of the present invention, the locking member 20 is a substantially U-shaped, bent metallic strip 22. While a metallic strip is disclosed in accordance with a preferred embodiment of the present invention, other materials may be used while remaining within the spirit of the present invention. As such, the locking member 20 includes a central base member 28 with first and second upwardly extending arms 24, 26. The first and second arms 24, 26 respectively include centrally located first and second needle apertures 30, 32. As will be better appreciated based upon the following disclosure, the apertures 30, 32 are shaped to be slightly larger than the needle 18 intended to pass therethrough. As such, when the first and second arms 24, 26 are close to parallel, the needle may freely slide within the first and second needle apertures 30, 32. However, when the first and second arms 24, 26 are moved toward each other and angled, the projection of the diameter of the first and second needle apertures 30, 32 that are perpendicular to the longitudinal axis of the needle 18 passing therethrough decreases, locking the needle 18 in position. More specifically, the metallic strip 22 is bent in the form of an open delta, that is, a substantially triangular shape with an open apex, including first and second upwardly extending arms 24, 26 connected by the central base member 28.

As mentioned above, the central base member 28 integrally links the first and second upwardly extending arms 24, 26. The apex of the delta forms an opening to accommodate positioning of the release member 34 therebetween in a manner that will be discussed below in greater detail.

In practice, the locking member 20 is biased toward a delta configuration such that the needle stick protection device 10 is locked on to the needle 18 at all times except when the release member 34 is activated to move the first and second upwardly extending arms 24, 26 to a substantially parallel position. More specifically, the needle locking force is provided by the bending induced in the metallic strip 22 when the needle 18 is positioned within the first and second needle apertures 30, 32 and the release member 34 is unactuated.

Figure 2:
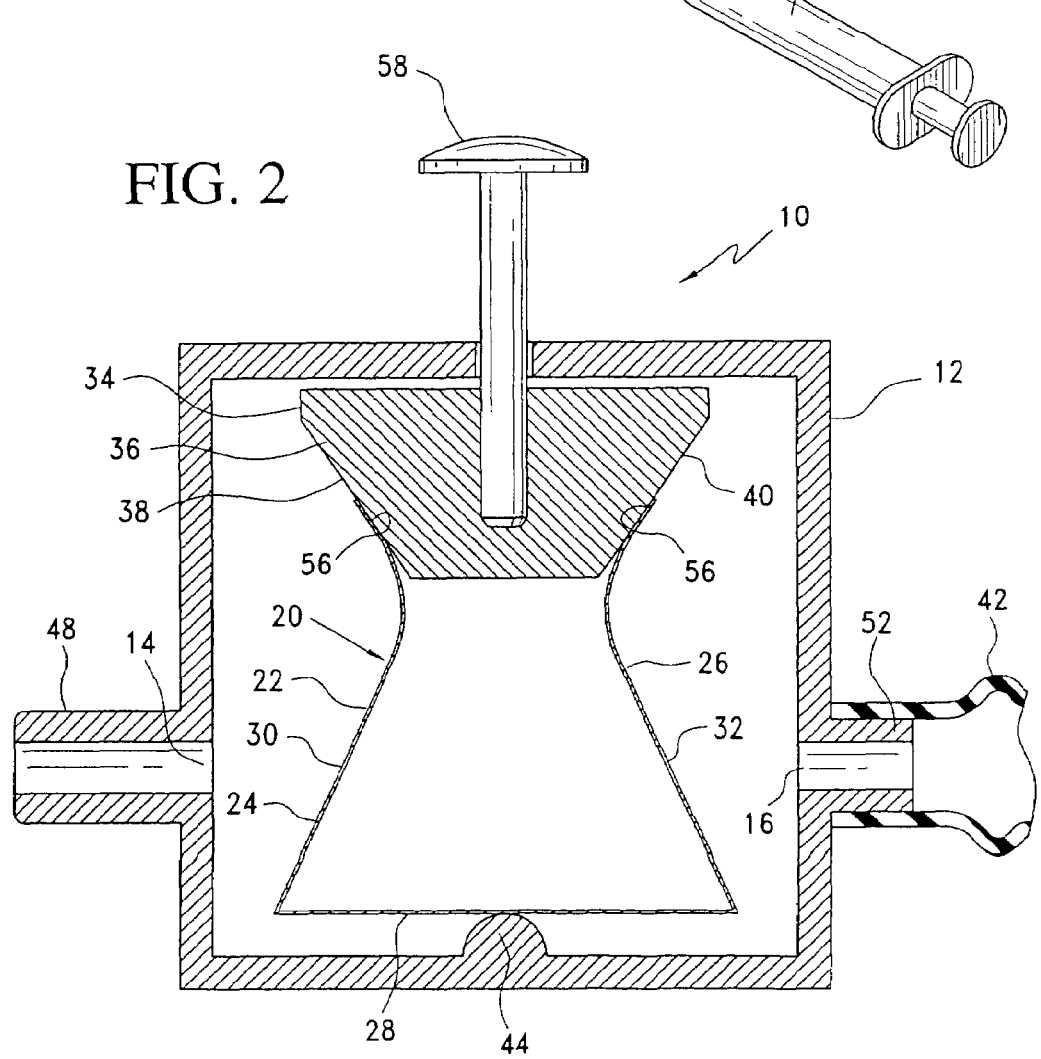
FIG. 2 is a cross section view of the needle stick protection device without the needle.
Figure 3:
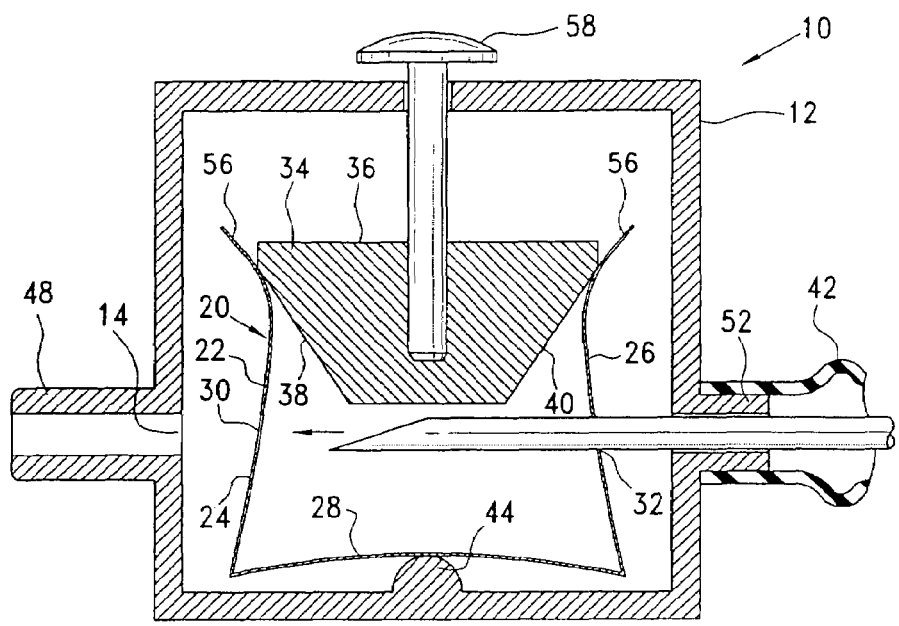
FIG. 3 is a cross section view with the needle stick protection device in its release position.
Figure 4:
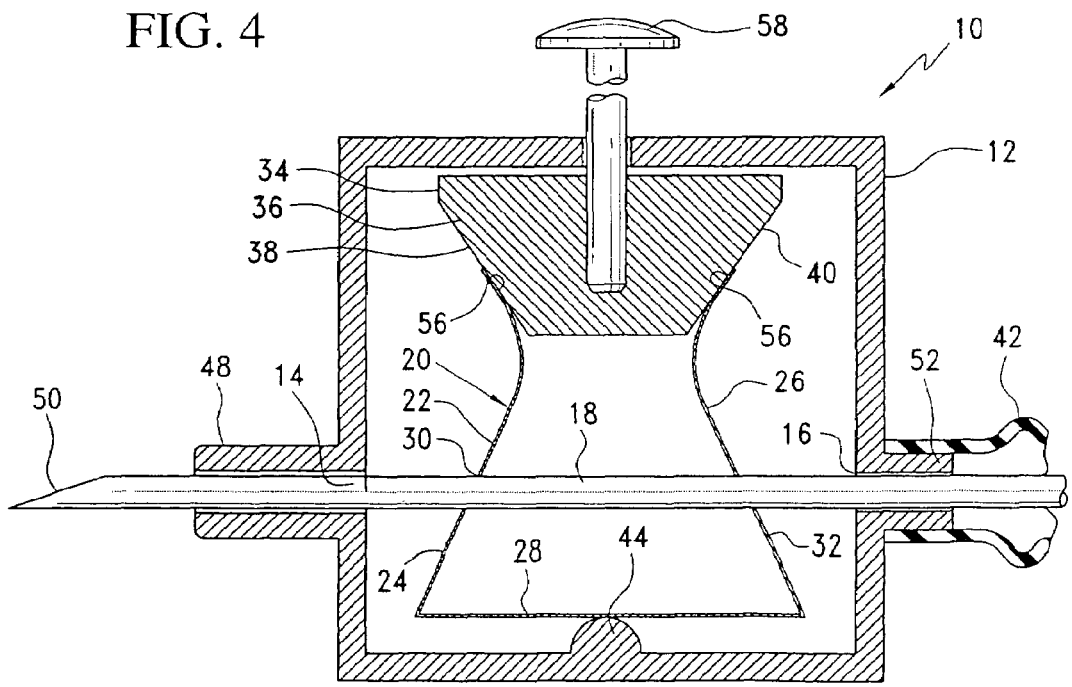
FIG. 4 is a cross section view of the needle stick protection device in its locking position.
Figure 5:
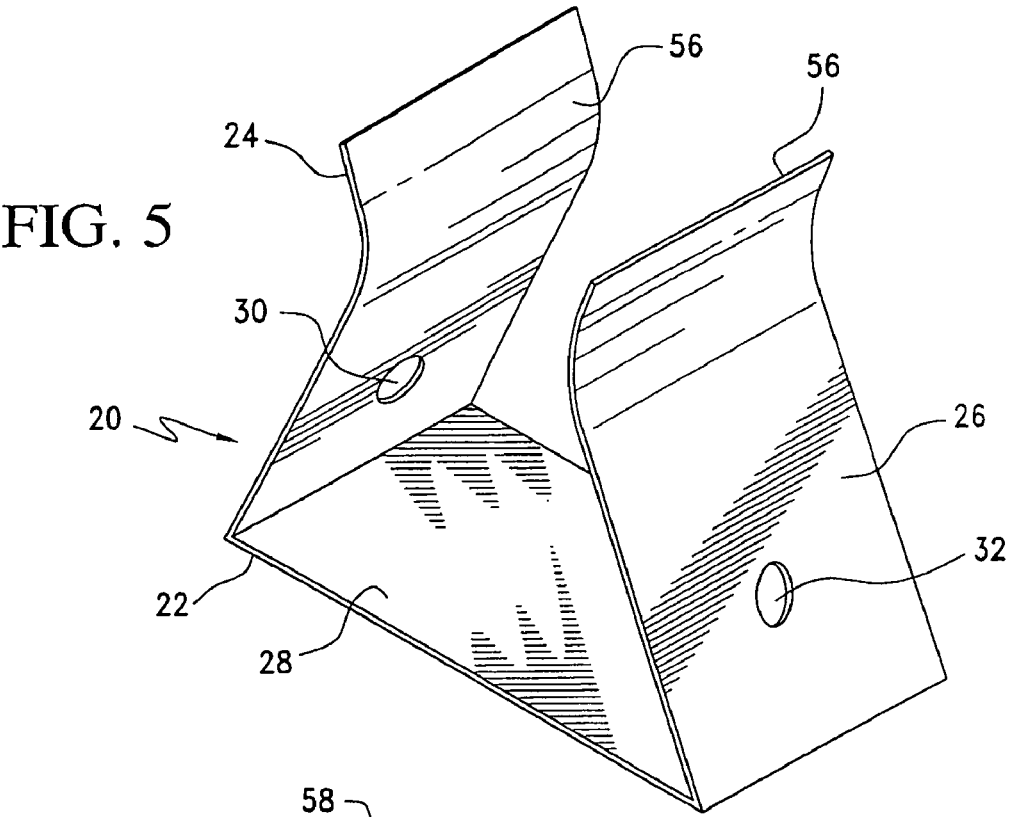
FIG. 5 is a perspective view of the locking member.
Figure 7:
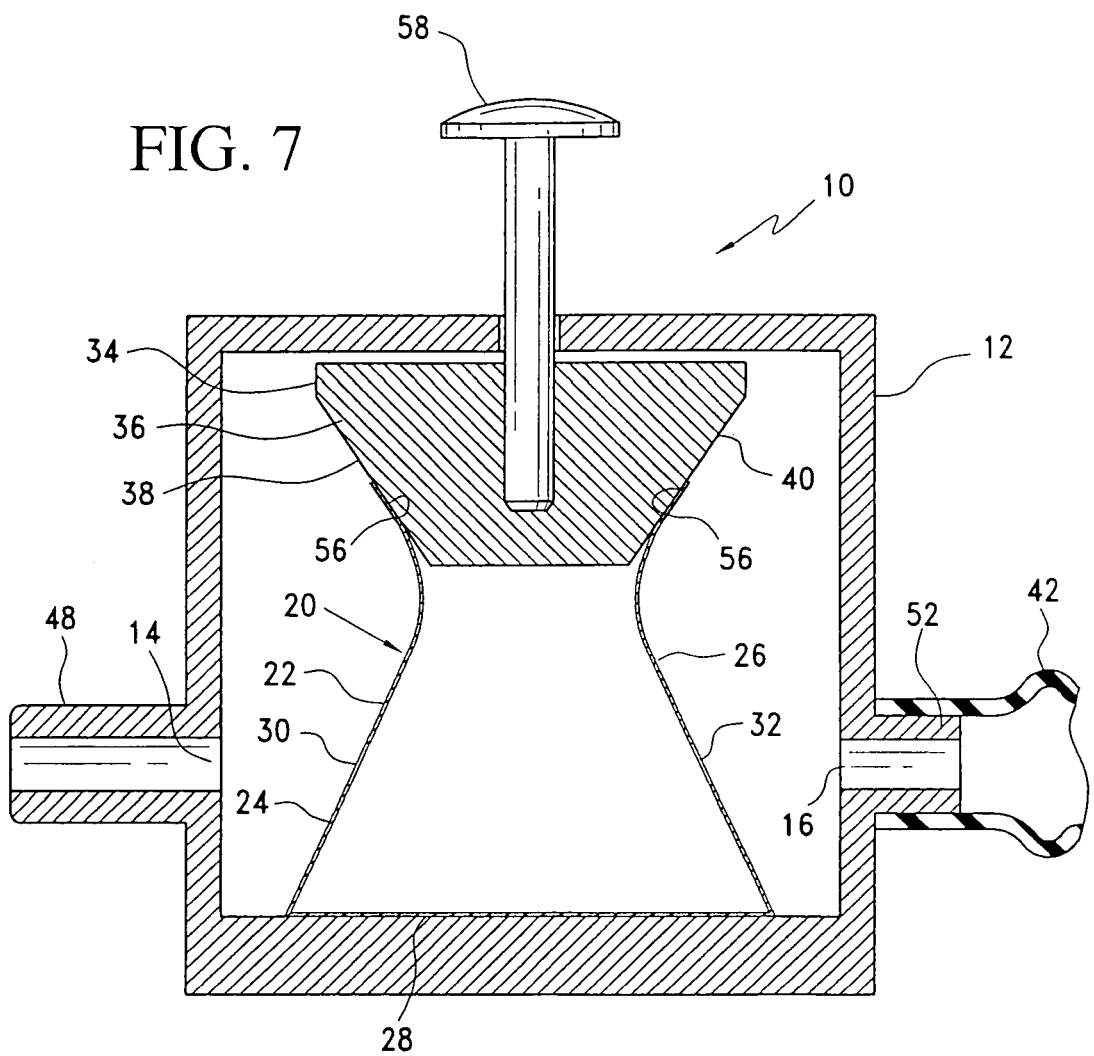
FIG. 7 is a cross sectional view of a needle stick protection device according to another alternate embodiment.

Functioning of the locking member 20 is further enhanced by the coupling of the metallic strip 22 to a projection 44 on the bottom of the housing 12. In accordance with an alternate embodiment, and as shown in FIG. 7, the metallic strip 22 may be supported along the entire length of the lower portion of the housing 12. By fixing the locking member 20 to the projections 44 as shown in FIGS. 2, 3 and 4, the finger pressure required to operate the release member 34 for release and movement of a needle 18 along the protection device 10 is reduced. However, the projections 44 similarly reduce the resulting contact pressure between the needle 18 and the locking member 20.

Fixing the locking member 20 along the entire length of the lower portion of the plastic housing 12 increases the finger pressure required to actuate the release member 34 and relocate the needle stick protection device 10 along a needle 18 and also increases the contact pressure between the needle 18 and the locking member 20, thereby enhancing the locking force on the needle 18.

Figure 6:
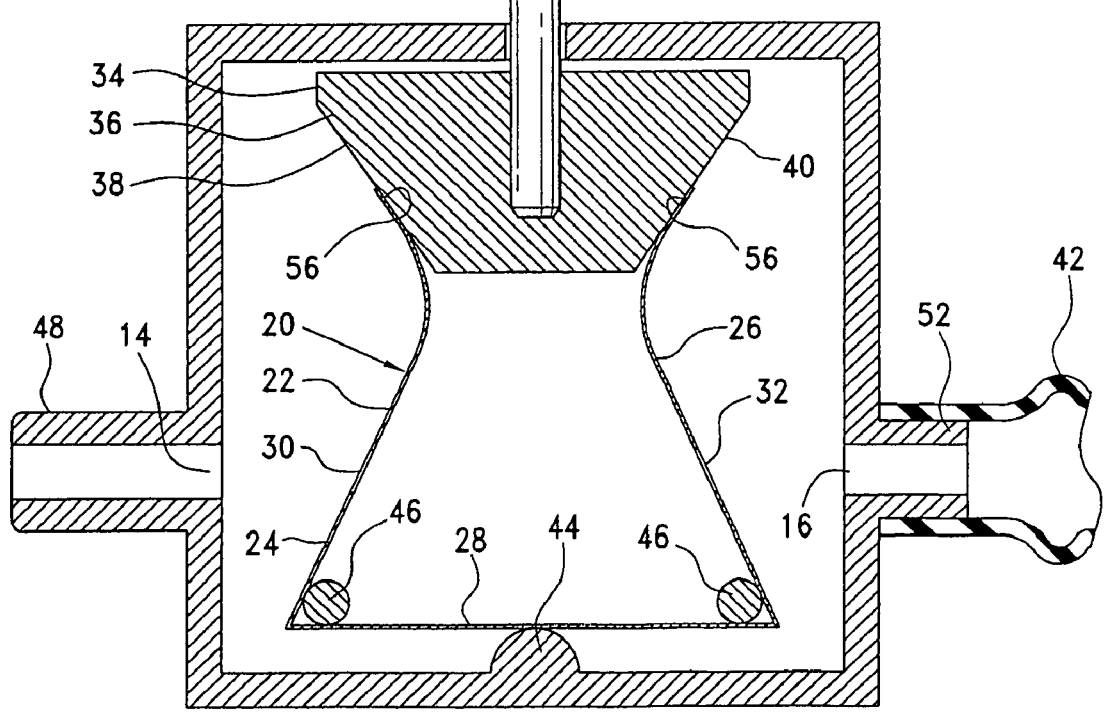
FIG. 6 is a cross sectional view of a needle stick protection device according to an alternate embodiment.

With reference to FIG. 6, it is further contemplated that the locking member 20 may be positioned on two pins 46 rather than only coupling the locking member 20 to the projections 44 as described above with regard to FIGS. 2, 3 and 4. The two pins 46 are positioned at the connection points of the central base member 28 with the first and second upwardly extending arms 24, 26 and help to control positioning of the locking member 20. However, and as those skilled in the art will certainly appreciate, there are a variety of ways in which the locking member may be mounted within the housing without departing from the spirit of the present invention.

As mentioned above, the protection device 10 further includes a housing 12 in which the operating components are maintained. The housing 12 is preferably constructed of molded plastic, although other material constructions may be employed without departing from the spirit of the present invention. In accordance with a preferred embodiment, the housing 12 is shaped and dimensioned for maintaining the locking member 20 and release member 34 therein. In addition, the housing 12 is provided with first and second apertures 14, 16 shaped and positioned for permitting the free passage of a needle 18 therethrough.

The housing 12 is further provided with a needle tip shield 48 composed of a tubular portion secured at one end of the housing member 12. The tip shield 48 shields a needle tip 50 without requiring that the needle 18 be pulled fully toward the center of the housing 12. The housing 12 further includes a bellows seal 42 at the opposite end. The bellows seal 42 is secured to a projection 52 extending adjacent the second aperture 16 of the housing 12. Shielding of the needle tip 50 is effected by sliding the needle stick protection device 10 as far as possible toward the tip 50 of the needle 18. The length of the inextensible bellows seal 42 controls the amount of sliding. When the bellows seal 42 is fully extending, the tip 50 of the needle 18 is inside the tip shield 48 of the housing 12. The inside diameter of the tip shield 48 of the housing 12 is only slightly larger than the outside diameter of the needle 18. The length of the tip shield 48 is such that body contact with the tip 50 of the needle 18 is impossible.

With regard to the release member 34, it is preferably a low friction, tapered plastic member. The release member includes a camming member 36 having tapered sides 38, 40 shaped and dimensioned for engaging camming surfaces 56 of the first and second upwardly extending arms 24, 26 of the locking member 20. The camming member 36 is coupled to a release button 58. The release button 58 extends through the upper surface of the housing 12 for engagement by a user of the present needle stick protection device 10.

In use, the release member 34 functions to disengage a needle 18 from the locking member 20 by forcing the camming member 36 to increase the size of the open end of the delta of the locking member 20. The camming member 36 engages the first upwardly extending arm 24 and the second upwardly extending arm 26 such that selective movement of the release member 34 causes the first and second upwardly extending arms 24, 26 to move between a first locking position in which the first and second upwardly extending arms 24, 26 are angled toward each other and a second release position in which the first and second upwardly extending arms 24, 26 are substantially parallel. More particularly, the geometry of the camming member 36 is such that the first and second upwardly extending arms 24, 26 of the locking member 20 approach parallelism as the release member 34 is forced downwardly in a manner extending the open end of the delta of the locking member 20. When a substantially parallel configuration is achieved, the needle 18 is free to slide within the first and second needle apertures 30, 32 of the first and second upwardly extending arms 24, 26.

As mentioned above, the housing 12 is provided with a bellows seal 42 that controls the extension of the housing 12 along the length of the needle 18. The bellows seal 42 is preferably composed of a thin, elastomeric tear resistant material. The bellows seal 42 is fastened to the housing 12 of the needle stick protection device 10 adjacent the second aperture 16 such that it extends between the needle protection device 10 and the syringe body 60. The bellows seal 42 is made inextensible by embedding inextensible cords therein. The cords limit the amount of movement the bellows seal 42 can attain. The bellows seal 42 prevents bodily contact with the portion of the needle 18 between the housing 12 and the syringe 60 while simultaneously providing sufficient axial travel to shield the tip 50 of the needle 18 against bodily contact. Although inextensible cords are described in accordance with a preferred embodiment of the present invention, those skilled in the art will appreciate that other structures may be employed without departing from the spirit of the present invention.

In operation, the needle stick protection device 10 is operated by squeezing the release button 58 and the bottom of the housing 12 between the thumb and forefinger. The camming member 36 of the release member 34 thereby forces the first and second upwardly extending arms 24, 26 toward a substantially parallel configuration, that is, toward a release position. By squeezing the needle stick protection device 10 in this manner the projected areas of the first and second needle apertures 30, 32 in planes perpendicular to the needle 18 are varied. Releasing the release button 58 removes the load on the locking member 20 and the locking member 20 attempts to return to its unloaded geometry, presenting a projected area to the needle 18 which is smaller than the transverse cross section of the needle 18 thereby "locking" the needle 18 in place. By varying the projected area of the first and second needle apertures 30, 32 in this manner, the needle stick protection device 10 can be made to lock and unlock the needle 18. Various design equations applied to the present invention allow the user to design a needle stick protection device for a selected needle outer diameter or for a range of needle diameters.

Since the needle stick protection device 10 is locked on to the needle 18 except when the release button 58 is depressed, the needle stick protection device 10 can also be used to limit the depth of needle penetration into the patient by moving the needle stick projection device 10 so that the desired needle length is exposed.

The needle stick protection device 10 is attached to the needle 18 by fully depressing the release button 58 and sliding the housing 12 over the needle 18. Fully depressing the release button 58 lines up the first and second needle apertures 30, 32 and the first and second apertures 14, 16 of the housing 12 so that the needle 18 can be inserted within the first and second apertures 14, 16, the first and second needle apertures 30, 32 and the housing 12. When the release button 58 is released, the locking member 30 attempts to return to its unloaded geometry. Since the transverse cross sectional area of the needle 18 is greater than the minimum projected area of the first and second needle apertures 30, 32 of the locking member 20, the locking member 20 cannot fully return to its unloaded geometry and instead, contacts the needle 18 at four locations. The contact force developed at the needle 18 with the locking member 20 is a function of the amount of bias remaining in the locking member 20 after the release button 58 is released and the area of the four small contact regions between the needle 18 and the needle apertures 30, 32. The contact force creates friction making it highly difficult for the needle 18 to be moved within the housing 12.

As those skilled in the art will appreciate, various design equations can be used to design a needle stick protection device 10 which will generate any desired contact force. Once the needle stick projection device 10 has been locked on to the needle 18 it remains at that location until the release button 58 is depressed and the needle stick protection device 10 is moved to a new location.

When a medical practitioner desires needle stick protection, the protection device 10 is moved toward the tip 50 of the needle 18 to the limit provided by the elastomeric bellows seal 42. At this location, the needle tip 50 is inside the tip shield 48 of the housing 12 and bodily contact is impossible. Limited penetration depth into a patient is achieved by moving the needle stick protection device 10 until a desired needle length is exposed. Thereafter, the release button 58 is released. The needle stick protection device 10 is fixed at that location and will limit the depth of penetration by making contact with the patient.

Figure 8:
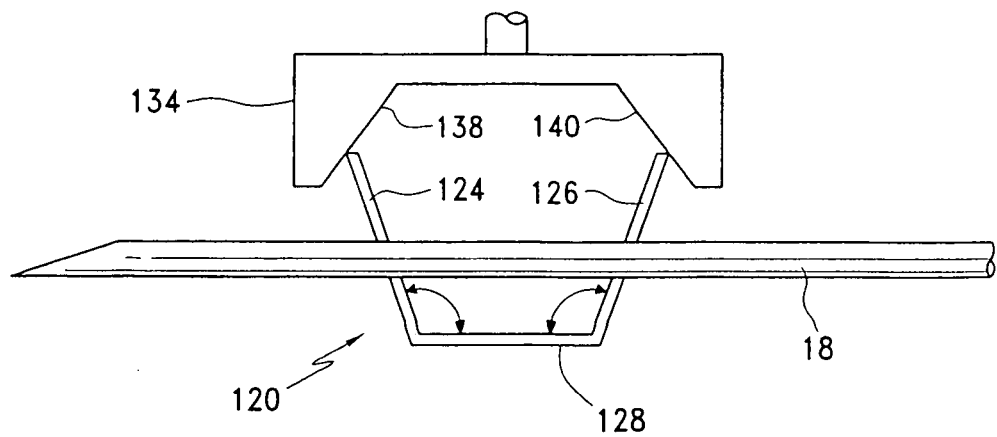
FIG. 8 is a cross sectional view of a needle stick protection device in accordance with an alternate embodiment.
Figure 9:
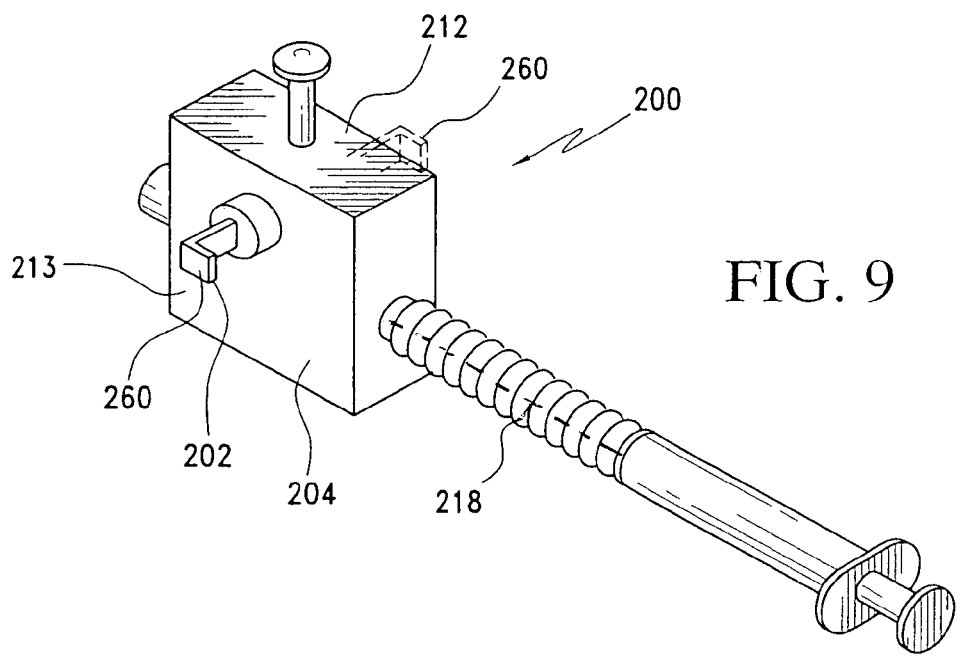
FIG. 9 is a perspective of a needle stick protection device in accordance with an alternate embodiment.
Figure 10:
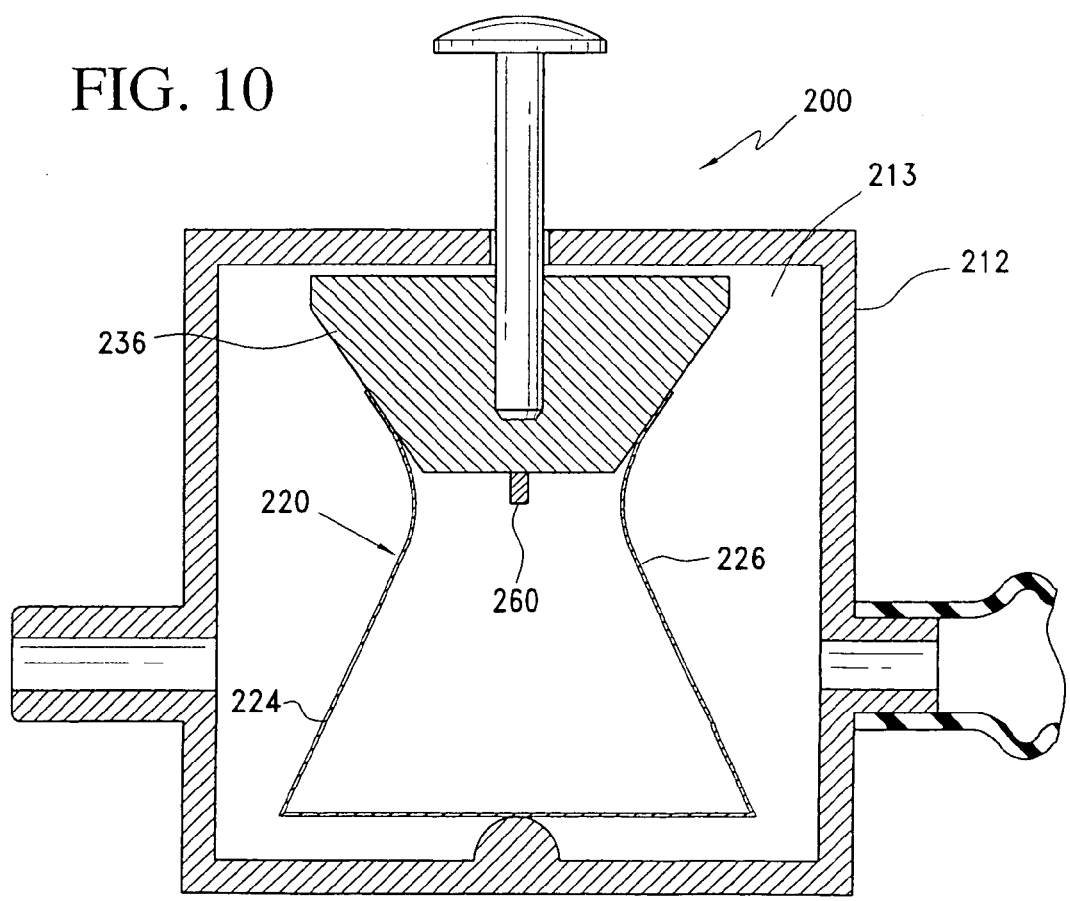
FIG. 10 is a cross sectional view of the needle stick protection device without the needle.

The locking member 20 described above is in the form of an open delta. As a result, the angles between the central base member 28 and the first and second upwardly extending arms 24, 26 are acute, i.e., the angles are less than 90 degrees. In accordance with an alternate embodiment, and with reference to FIG. 8, the locking member 120 may have obtuse angles between the central base member 128 and the first and second upwardly extending arms 124, 126, i.e., the angles are greater than 90 degrees. In accordance with this embodiment, the resulting geometry of the locking member 120 is in the form of an open channel in which the distance between the ends of the first and second upwardly extending arms 124, 126 is greater than the length of the central base member 128. The release member 134 is similarly shaped with inwardly facing tapered sides 138, 140 shaped and dimensioned for engaging the first and second upwardly extending arms 124, 126 as discussed above with regard to the earlier embodiments.

Referring to FIGS. 9 to 13, another embodiment of a needle stick protection device 200 in accordance with the spirit of the present invention is disclosed. The needle stick protection device described above with reference to FIGS. 1-8 allows for repeated shielding and unshielding of the needle during a procedure on a patient. As those skilled in the art will appreciate, there are times when it is necessary to permanently shield the needle such that it may not be utilized again. This embodiment provides a mechanism for doing such in conjunction with a needle stick protection device similar to that described above. Once the needle 218 is locked in its shielded position in accordance with the features of this embodiment, the needle 218 is ready for disposal using conventional techniques.

As discussed above, shielding and unshielding as described above is achieved by actuating a camming member 236 for movement within a locking member 220. Briefly, when the legs 224, 226 of the locking member 220 are angled toward each other, the needle stick protection device 200 is locked onto the needle 218 and the needle stick protection device 200 cannot be moved relative to the needle 218. When the camming member 236 is moved downwardly relative to the locking member 220, the first and second upwardly extending arms 224, 226 are moved toward a parallel orientation unlocking the needle stick protection device 200 from the needle 218 and allowing the needle stick protection device 210 to be moved along the longitudinal axis of the needle 218.

The embodiment described in FIGS. 9 to 13 presents a mechanism for permanently preventing movement of the camming member 236 such that the needle stick protection device 200 may be permanently locked for disposal. In accordance with this embodiment, the housing 212 is provided with one or more self-locking members 260 shaped and dimensioned for interfering with the movement of the camming member 236. The self-locking members 260 are moved relative to the housing 212 in a manner locking the camming member 236 of the needle stick protection device 200 so that it cannot be depressed to release the needle stick protection device 200 from the needle 218 and the needle stick protection device 200 is thereby permanently locked and ready for disposal.

In accordance with a preferred embodiment, and as described herein, two self-locking members 260 are provided in the housing 212 of the needle stick protection device 200. The self-locking members 260 are positioned on opposite sides of the housing 212 and are designed to slide under the camming member 236 in a plane perpendicular to the center line of the needle 218. The self-locking members 260 are collinear and preferably, rectangular.

Figure 11A:
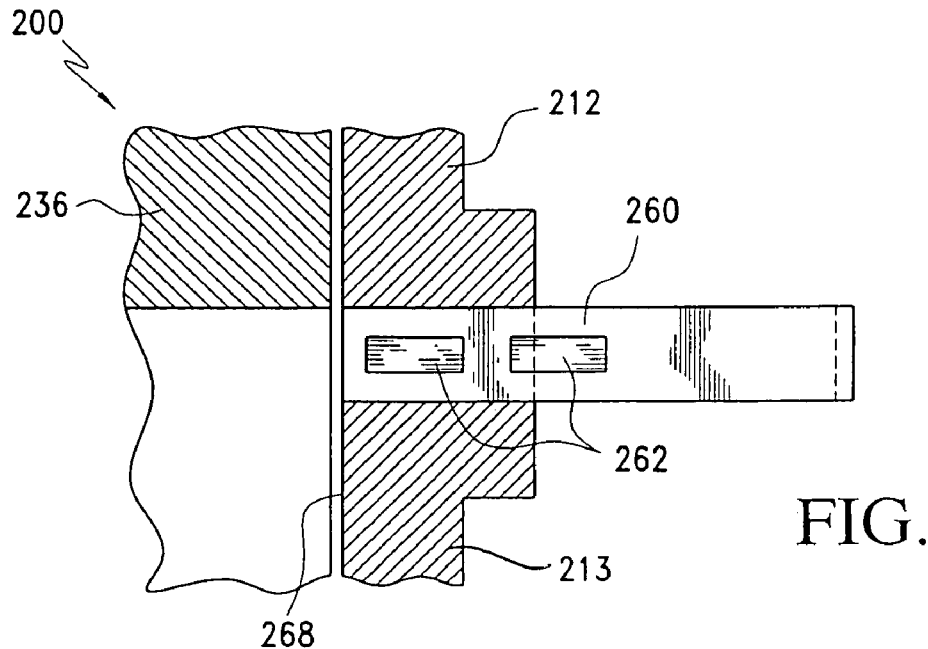
FIGS. 11A and 11B are cross sectional views respectively showing the self-locking member in its non-actuate position and actuated position.
Figure 11B:
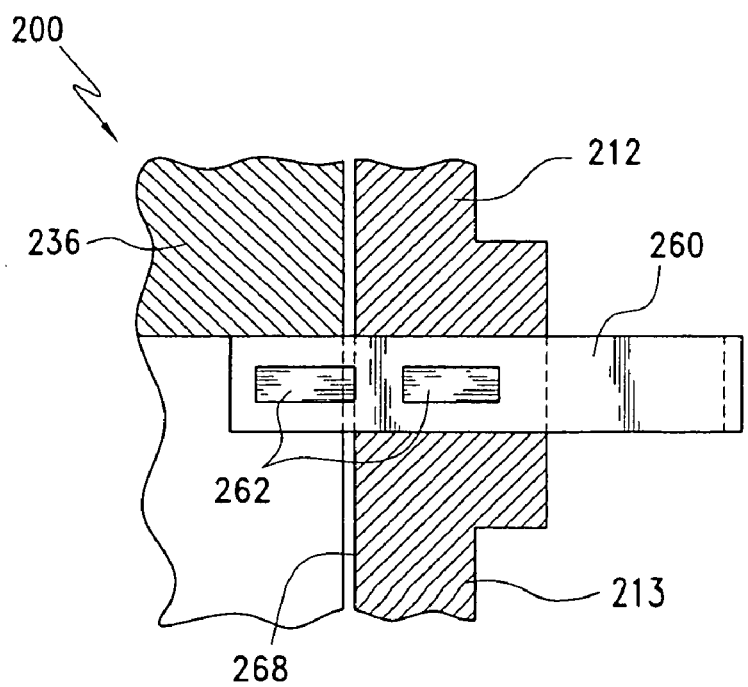
Figure 12:
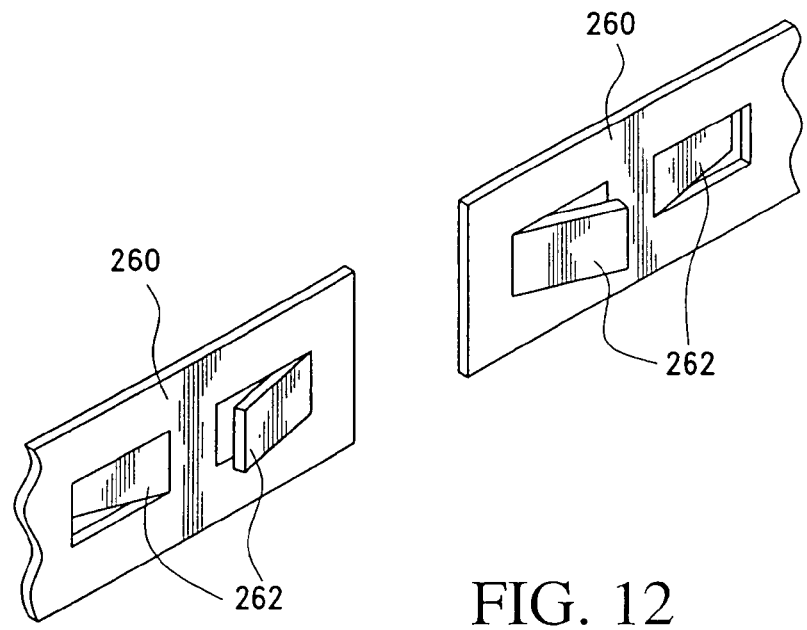
FIGS. 12 and 13 are respectively a perspective view and a side view of the self-locking members.

More particularly, and with reference to FIGS. 11A and 11B, the needle stick protection device 200 includes a first self-locking member 260 that is mounted on a side wall 213 of the housing 212 of needle stick protection device 200 such that it projects outwardly for engagement by the user. Although only the first self-locking 260 member is shown with reference to FIGS. 11A and 11B, the other self-locking member is substantially identical in structure and function. The self-locking member 260 is generally rectangular in shape and includes a plurality of locking tabs 262 that are spring biased outwardly from the plane of the longitudinal axis of the self-locking member 260.

In accordance with a preferred embodiment, the locking members 260 are made of metal or resilient plastic of sufficient strength for its intended purpose. However, those skilled in the art will appreciate that a variety of known materials may be used in the construction of the present needle stick protection device without departing from the spirit of the present invention.

Figure 13:
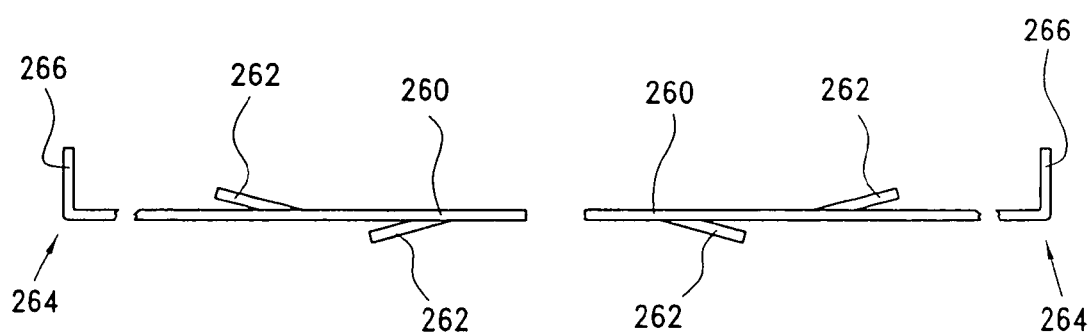

Referring to FIGS. 11A, 11B and 13, the proximal end 264 of the first self-locking member 260 is bent over to form a finger contact 266. The finger contact 266 facilitates inserting the self-locking member 260 into the needle stick protection device 200 as described herein below. FIG. 11A illustrates the first self-locking member 260 in the non-actuated position located in the wall 213 of the housing 212 of the needle stick protection device 200. In this position, the self-locking member 260 does not extend into the interior of the housing 212 of the needle stick protection device 200 allowing free up and down movement of the camming member 236. FIG. 11B illustrates the self-locking member 262 in an actuated position whereby it extends into the interior of the housing 212 of the needle stick protection device 200 and blocks downward movement of the camming member 236, it being appreciated only a portion of the camming member 236 is shown. The self-locking member 260 is locked in this position by the spring biased locking tabs 262 that engage the inner wall surface 268 of the housing 212 of the needle stick protection device 200. The self-locking member 260 is prevented from being pulled out of the side wall 213 of the housing 212 of the needle stick protection device 200 by the locking tabs 262 thus permanently grasping the needle and protecting the tip thereof as described in detail hereinabove.

In use, the needle stick protection device 200 is locked and unlocked relative to the needle 218 as described above with reference to the embodiments disclosed in FIGS. 1-8. However, when it is desired to permanently lock the needle stick protection device 200 upon the needle 218, the self-locking members 260 are forced inwardly toward the center of the housing 212. As they move forward, they slide under the camming member 236. The self-locking members 260 are locked in position by the spring biased locking tabs 262 which extend outwardly and engage the inner wall surface 268 of the housing 212 to prevent retraction of the self-locking members 260 and maintain them in position preventing downward movement of the camming member 236 in a manner that would unlock the needle relative to the needle stick protection device 200.

Although a preferred embodiment disclosed herein employs two self-locking members, it is contemplated that one or more self-locking members may be utilized without departing from the spirit of the invention.

Although the needle stick protection device herein is directed primarily to the medical field, those skilled in the art will appreciate the basic concept can be applied to many other fields. For example, the first and second needle apertures formed in the first and second upwardly extending arms are circular, since the medical needles for which it is designed have circular cross sections. However, the first and second apertures in the first and second upwardly extending arms need not have the same cross sectional geometry as the shaft, or other element, which is to be locked and passed through the first and second apertures. The requirement for locking is that when the first and second upwardly extending arms contact the shaft passing through the first and second apertures, the length of the first and second apertures perpendicular to the longitudinal axis of the shaft are less than the length of the cross sectional dimension of the shaft at that location. For example, the first and second apertures may be circular and the cross section of the shaft may be elliptical or any other geometry. Those skilled in the art will appreciate that the device described herein may be applied to all linkages that must be securely locked and easily unlocked for repositioning of the locked length of the shaft. In addition, the self-locking member 260 and/or the locking tabs may take a variety of different shapes.

With reference to FIG. 14, an alternate embodiment for a needle stick protection device 300 is disclosed. In accordance with this embodiment, the spring biased, first and second legs 324, 326 of the locking member 320 are integrally formed with the housing 312. It is contemplated, the first and second legs 324, 326 will either be formed of the same material as the housing 312 or that the first and second legs 324, 326 will be separately formed and co-molded with the housing 312 such that they are implanted within the material of the housing 312. Other than the formation of the first and second legs 324, 326 of the locking member 320 integrally with the housing 312, and consequently the removal of a central base member connecting the first and second arms 324, 326, this needle stick protection device 300 functions substantially the same as that disclosed with reference to FIGS. 9-13. As such, one is referred to the preceding discussion for an in depth discussion of the other structure and the functionality thereof.

While the preferred embodiments have been shown and described, it will be understood that there is no intent to limit the invention by such disclosure, but rather, is intended to cover all modifications and alternate constructions falling within the spirit and scope of the invention, as defined in the appended claims.

The invention claimed is:

1. A needle stick protection device, comprising:

a housing;

a locking member positioned within the housing to permit the selective locking of the needle relative to the housing, the locking member comprising spring biased, first and second upwardly extending arms, the first and second upwardly extending arms being biased relative to each other and respectively including a first needle aperture and second needle aperture;

a release member associated with the locking member for facilitating the controlled release of a needle locked in position by the locking member, the release member engaging the first upwardly extending arm and the second upwardly extending arm such that selective movement of the release member causes the first and second upwardly extending arms to move between a first locking position in which the first and second upwardly extending arms are angled relative to each other and a second release position in which the first and second upwardly extending arms are substantially parallel;

wherein the first and second needle apertures are oriented to permit the free passage of a needle therethrough when the locking member is in its second release position and the first and second needle apertures are oriented to lock the needle relative to the locking member when the first and second upwardly extending arms are in their first locking position; and a self-locking member to permanently lock the needle within the housing, and wherein the self-locking member extends through the housing for selective engagement with the release member preventing movement of the release member from the first locking position to the second release position.

2. The needle stick protection device according to claim 1, wherein the self-locking member cooperates with an opening in the housing.

3. The needle stick protection device according to claim 1, wherein the self-locking member is longitudinal in shape and includes a plurality if spring biased locking tabs along the length thereof, the spring biased locking tabs extending outwardly from the longitudinal axis of the self-locking member.

4. The needle stick protection device according to claim 3, wherein the locking tabs engage inner wall surfaces of the housing in a locked position.

5. The needle stick protection device according to claim 3, wherein the self-locking member further includes a finger contact at a distal end thereof to facilitate insertion into the housing.

6. A syringe, comprising:

a syringe body having a needle extending therefrom;

a needle stick protection device selectively secured to the syringe, the protection device including:

a housing;

a locking member positioned within the housing to permit the selective locking of the needle relative to the housing, the locking member comprising spring biased, first and second upwardly extending arms, the first and second upwardly extending arms being biased relative to each other and respectively including a first needle aperture and second needle aperture;

a release member associated with the locking member for facilitating the controlled release of a needle locked in positioned by the locking member, the release member engaging the first upwardly extending arm and the second upwardly extending arm such that selective movement of the release member causes the first and second upwardly extending arms to move between a first locking position in which the first and second upwardly extending arms are angled relative to each other and a second release position in which the first and second upwardly extending arms are substantially parallel;

wherein the first and second needle apertures are oriented to permit the free passage of a needle therethrough when the locking member is in its second release position and the first and second needle apertures are oriented to lock the needle relative to the locking member when the first and second upwardly extending arms are in their first locking position; and a self-locking member cooperating with an opening in the housing, the self-locking member being longitudinal in shape and including a plurality if spring biased locking tabs along the length thereof: the spring biased locking tabs extending outwardly from the longitudinal axis of the locking member, wherein the locking tabs engage inner wall surfaces of the housing in a locked position preventing removal of the self-locking member from the housing, and wherein the self-locking member extends through the housing for selective engagement with the release member preventing movement of the release member from the first locking position to the second release position.

7. The needle stick protection device according to claim 6, wherein the self-locking member further includes a finger contact at a distal end thereof to facilitate insertion into the housing.

8. The needle stick protection device according to claim 6, wherein the locking member the first and second upwardly extending arms are connected by a central base member.

9. The needle stick protection device according to claim 6, wherein the first and second upwardly extending arms are integrally formed with the housing.

\* \* \* \* \*